(12) United States Patent
Ishikawa et al.

(10) Patent No.: US 8,783,521 B2
(45) Date of Patent: Jul. 22, 2014

(54) CONTAINER FOR EYE DROPS

(75) Inventors: Shinichi Ishikawa, Osaka (JP); Yuji Sugahara, Osaka (JP); Hiroyuki Yamazaki, Osaka (JP); Shintaro Adachi, Tokushima (JP); Yusuke Ogawa, Tokushima (JP); Kousuke Toujou, Tokushima (JP); Yoshiteru Ishikawa, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 80 days.

(21) Appl. No.: 13/321,806

(22) PCT Filed: May 21, 2010

(86) PCT No.: PCT/JP2010/058609
§ 371 (c)(1),
(2), (4) Date: Nov. 21, 2011

(87) PCT Pub. No.: WO2010/134590
PCT Pub. Date: Nov. 25, 2010

(65) Prior Publication Data
US 2012/0067926 A1    Mar. 22, 2012

(30) Foreign Application Priority Data
May 22, 2009 (JP) ................................. 2009-124536

(51) Int. Cl.
*B65D 37/00* (2006.01)

(52) U.S. Cl.
USPC ........... 222/213; 222/407; 222/422; 222/496; 222/518; 222/549; 604/294; 137/859; 239/327; 239/459; 239/576

(58) Field of Classification Search
USPC ............ 222/189.09, 212–213, 406–407, 422, 222/494–497, 518, 547, 549; 239/327, 459, 239/570, 576; 604/294–300; 137/859
See application file for complete search history.

(56) References Cited

U.S. PATENT DOCUMENTS 1,971,371 A * 8/1934 Donnelly .................... 222/493
3,913,803 A * 10/1975 Laauwe ................... 222/402.11
(Continued)

FOREIGN PATENT DOCUMENTS

JP    51-68746    5/1976
JP    2-63359     5/1990
(Continued)

OTHER PUBLICATIONS

International Search Report from the Japanese Patent Office for International Application No. PCT/JP2010/058609, mailing date Jul. 13, 2010.

(Continued)

*Primary Examiner* — Paul R Durand
*Assistant Examiner* — Andrew P Bainbridge
(74) *Attorney, Agent, or Firm* — Finnegan, Henderson, Farabow, Garrett & Dunner, L.L.P.

(57) ABSTRACT

A flexible and restorable container main body for housing a medicinal solution. A stopper member is fixed in an inside of a medicinal solution passage that communicates with the container main body for discharging the medicinal solution when the container main body is pressed and deformed. A pressure valve is arranged in the medicinal solution passage at a downstream side in the medicinal solution discharge direction further than the stopper member and is formed with an opening having a circular cross section which contacts a tip portion of the stopper member. A biasing member is provided at a downstream side for biasing the pressure valve in a direction opposite to the medicinal solution discharge direction by abutting against a peripheral portion of the opening of the pressure valve.

18 Claims, 13 Drawing Sheets

(56) References Cited

U.S. PATENT DOCUMENTS

| | | | |
|---|---|---|---|
| 5,074,440 A * | 12/1991 | Clements et al. | 222/189.09 |
| 5,992,764 A | 11/1999 | Bougamont et al. | |
| 6,672,479 B2 * | 1/2004 | Shiraishi et al. | 222/105 |
| 6,974,053 B2 * | 12/2005 | Lautre et al. | 222/92 |
| 7,225,949 B2 * | 6/2007 | Kubo et al. | 222/189.08 |
| 2006/0043116 A1 | 3/2006 | Kawashiro et al. | |
| 2009/0318883 A1 | 12/2009 | Sugahara et al. | |

FOREIGN PATENT DOCUMENTS

| | | |
|---|---|---|
| JP | 2000-025814 | 1/2000 |
| JP | 2000-502978 | 3/2000 |
| JP | 2007-015739 | 1/2007 |
| WO | WO 97/25253 | 7/1997 |
| WO | WO 2004/011345 A1 | 2/2004 |
| WO | WO 2007/111256 A1 | 10/2007 |

OTHER PUBLICATIONS

International Preliminary Report on Patentability dated Dec. 22, 2011 issued in corresponding International Application No. PCT/JP2010/058609.

* cited by examiner

FIG. 20
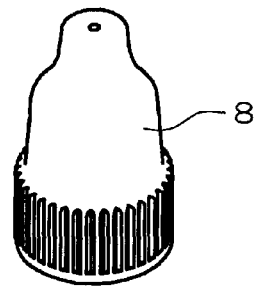
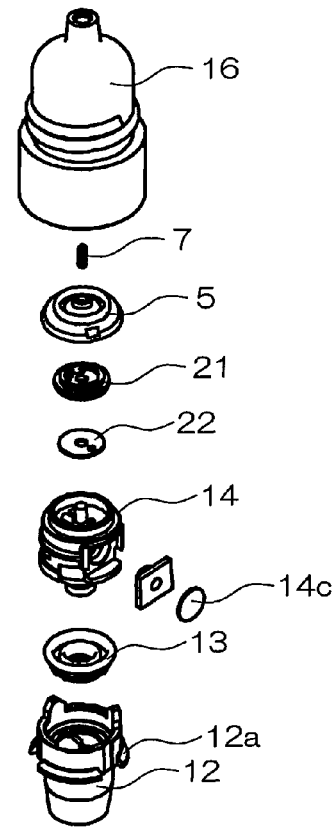
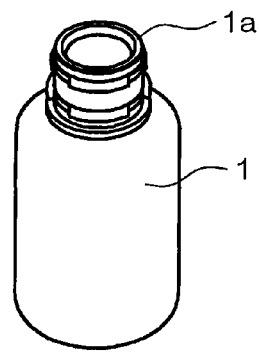

CONTAINER FOR EYE DROPS

TECHNICAL FIELD

The present invention relates to a container for eye drops that houses a medicinal solution in a container main body and discharges the medicinal solution when the container main body is pressed and deformed.

BACKGROUND ART

Conventionally, containers have been used for eye drops including flexible container main bodies that house medicinal solutions and spouts that are provided on the container main bodies and for discharging the medicinal solutions housed therein.

In such a container, the medicinal solution is discharged from the spout when the container main body is pressed and deformed, so that the container main body reaches an internal pressure higher than the atmospheric pressure. Then, outside air is made to flow in from the spout of the container main body when the container main body is released from pressing, and the container main body reaches an internal pressure lower than the atmospheric pressure, so as to restore the container main body into the shape before pressing.

However, in such a container, normally, since pathogenic microorganisms such as fungi and viruses exist in outside air that flows into the container, there is a problem that the medicinal solution housed in the medicinal solution container is contaminated with such outside air.

Therefore, as a container for solving such a problem, known is a container including (1) a flexible container main body that houses a medicinal solution, (2) a discharge portion that is provided on the container main body and is for discharging the medicinal solution housed in the container main body when the container main body is pressed and deformed and the container main body reaches an internal pressure higher than the atmospheric pressure, (3) a check valve portion that is communicated with the exterior of the container main body and is for making outside air flow in the interior of the container main body when the container main body is released from pressing and the internal pressure of the container main body reaches a negative pressure. The check valve portion is designed for preventing the medicinal solution in the interior of the container main body from leaking when the internal pressure of the container main body reaches a positive pressure. And (4) a filter portion is provided at an upstream side further than the check valve portion in the flow-in direction of outside air in the container main body for purifying the outside air that flows in the check valve portion.

According to such a configuration, when the container main body is released from pressing and the container main body reaches an internal pressure lower than the atmospheric pressure, outside air passes through the filter portion, and is then made to flow in the interior of the container main body via the check valve. Therefore, since the outside air that flows in the container main body after releasing from pressing is purified by the filter portion, contamination of the medicinal solution housed in the container main body can be efficiently prevented.

Meanwhile, the spout of the container for eye drops according to the prior art has a function of a so-called pressure valve. The pressure valve is closed if a fluid pressure is not received from an upstream side in the discharge direction, and is opened to discharge a medicinal solution from the opening of the pressure valve when the fluid pressure is received from an upstream side in the discharge direction (Patent Documents 1 and 2 in the following). Due to this function, the opening of the pressure valve is blocked when the container main body is released from pressing and the container main body reaches an internal pressure lower than the atmospheric pressure, so that outside air and the medicinal solution remaining in the periphery of the opening of the pressure valve can be prevented from entering into the interior of the container main body.

Patent Document 1: Japanese Published Unexamined Patent Application No. JP2007-15739A
Patent Document 2: International Publication No. WO07/111256 Pamphlet
Patent Document 3: International Publication No. WO97/25253 Pamphlet
Patent Document 4: Publication of national Application No. JP2000-502978A (translation from Patent Document 3)

SUMMARY OF INVENTION

In the container for eye drops according to the prior art, since the pressure valve is required to be easily deformed by a fluid pressure due to pressing of the container main body, a material has been used whose hardness is low and flexibility is high, such as an elastomer.

However, after production, since the material of the pressure valve deteriorates with time, leakage of the solution may occur as a result of the opening of the pressure valve that is not completely blocked from the opening of the pressure valve after the medicinal solution is discharged. Moreover, besides the deterioration of the material of the pressure valve, the pressure valve itself may have a shape error, and the attached state of the pressure valve may not be as designed. These factors also cause an occurrence of leakage of the solution.

On the other hand, when a hard material is used for the pressure valve to prevent leakage of the solution, a great force is required to discharge the medicinal solution from the opening of the pressure valve, so that usability is reduced.

Therefore, there has been a demand for a container for eye drops that allows a medicinal solution to fall in drops when the container is directly pressed with a weak force and can prevent leakage of the solution from an opening of a pressure valve when the container is restored.

A container for eye drops of the present invention includes a flexible and restorable container main body for housing a medicinal solution, a medicinal solution passage that is communicated with the container main body and is for discharging the medicinal solution housed in the container main body when the container main body is pressed and deformed, a stopper member that is fixed in the inside of the medicinal solution passage and has its tip portion at a downstream side in a medicinal solution discharge direction. The tip portion has a predetermined-shaped cross section when viewed from the medicinal solution discharge direction. The container further includes a pressure valve which is arranged in the medicinal solution passage at a downstream side in the medicinal solution discharge direction further than the tip portion of the stopper member, and is formed with an opening having a predetermined-shaped cross section that contacts the tip portion, and a biasing member that is provided in the medicinal solution passage at a downstream side in the medicinal solution discharge direction further than the pressure valve, and is for biasing the pressure valve in a direction opposite to the medicinal solution discharge direction by abutting against a peripheral portion of the opening of the pressure valve.

In the container for eye drops according to the present invention, the container main body is pressed for discharging of a medicinal solution from the opening. By such an operation, a fluid pressure is applied to the medicinal solution housed in the container main body, and the medicinal solution introduced from an upstream side of the pressure valve is discharged through a gap between the pressure valve and the stopper member.

When the container main body is released from pressing and is restored, it is necessary to prevent the medicinal solution remaining in the medicinal solution passage from leaking out through the gap between the pressure valve and the stopper member. For that purpose, the biasing member is provided in the present invention. That is, since the biasing member abuts against the peripheral portion of the opening of the pressure valve, and biases the pressure valve in a direction opposite to the medicinal solution discharge direction to press the pressure valve against the tip portion of the stopper member, leakage of the medicinal solution remaining in the medicinal solution passage can be reliably prevented.

This configuration of the present invention is different from the configuration of the container for eye drops described in Patent Document 3 in that the configuration of the invention including a stopper member fixed to the inside of the medicinal solution passage and having a tip portion at a downstream side in its medicinal solution discharge direction, and in that a pressure valve is disposed at a downstream side in the medicinal solution discharge direction further than the tip portion.

According to the present invention, by biasing the pressure valve by the biasing member to press the pressure valve against the tip portion of the stopper member, the stopper member can be uniformly sealed with a weak biasing force.

If the tip portion has a circular cross section when viewed from the medicinal solution discharge direction, the shape of the tip portion of the stopper member is preferably a hemispherical shape or a conical shape in order to abut against a circular opening of the pressure valve without a gap.

Also it is preferable that of the opening of the pressure valve, a part which contacts the tip portion of the stopper member makes line contact in a ring shape with the tip portion of the stopper member, and the contact part has a circular longitudinal section. Since a line that contacts the tip portion of the stopper member has a ring shape or a circumferential shape when viewed in section from the medicinal solution discharge direction, contact without leakage is realized.

The biasing member may be directly abutted against the peripheral portion of the opening of the pressure valve, or may be molded integrally with an opening portion of the pressure valve, or may be abutted against the peripheral portion of the opening of the pressure valve via a seat. In any case, the biasing member can bias the pressure valve in a direction opposite to the medicinal solution discharge direction. In the case of directly abutting against, biasing against the pressure valve can be realized by a very simple configuration. In the case of abutting against via a seat, designing the shape of the seat makes it easier to even the distribution of the biasing force by the pressure valve.

It is preferable that the container for eye drops of the present invention further includes an air flow passage that is communicated with an exterior of the container main body, and causes outside air to flow in an interior of the container main body when the container main body is released from pressing and is restored, and a filter portion that is provided in the air flow passage, for purifying outside air to flow in. The above container main body can take in fresh air through the filter portion and the air flow passage, when the container main body is released from pressing and the container main body reaches an internal pressure lower than the atmospheric pressure.

Also the container for eye drops of the present invention preferably includes a check valve portion that is provided in the air flow passage, and closes the air flow passage when an internal pressure of the container main body reaches a positive pressure. The check valve portion can prevent the filter portion from being wet by the medicinal solution, and thus air permeability is not degraded when the container main body is pressed.

Also in the container for eye drops of the present invention, a second filter portion may be disposed, in the medicinal solution passage, at an upstream side in the medicinal solution discharge direction further than the pressure valve in order to block foreign substances and particles that are permissible for eye drops from reaching the pressure valve. This construction prevents the foreign substances and particles from being caught between the pressure valve and the stopper member to hinder the function of the pressure valve.

According to the present invention, by placing a biasing member, the medicinal solution in the container main body can be discharged with a relatively weak force of only pressing the container main body, and leakage of the medicinal solution from the opening of the pressure valve can be prevented when the container main body is not pressed or released from pressing.

The above and other advantages, features, and effects of the present invention will become apparent through the following description of embodiments with reference to the accompanying drawings.

BRIEF DESCRIPTION OF DRAWINGS

FIG. 20 is an exploded perspective view of the container for eye drops.

DESCRIPTION OF EMBODIMENTS

Hereinafter, embodiments of the present invention will be described in detail with reference to the accompanying drawings.

Figure 1:
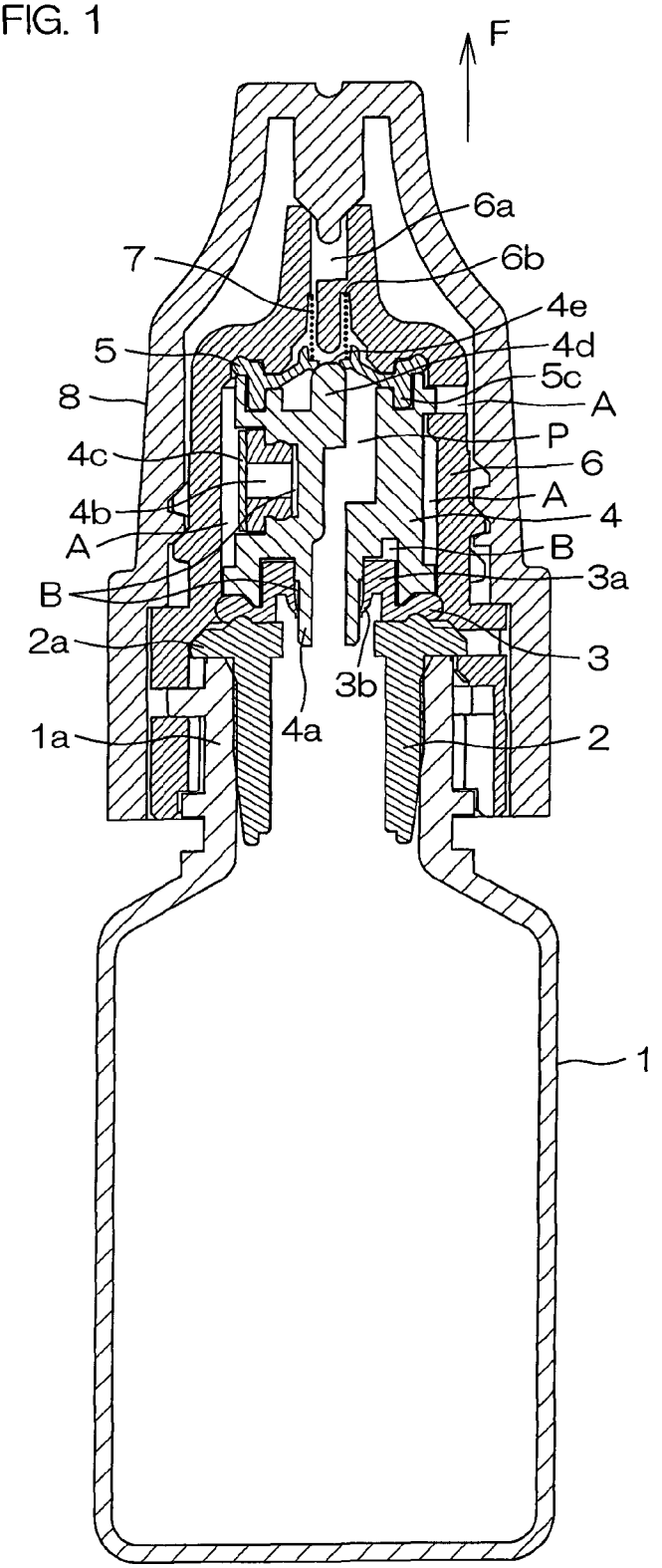
FIG. 1 is a sectional view showing a container for eye drops according to an embodiment of the present invention.
Figure 2:
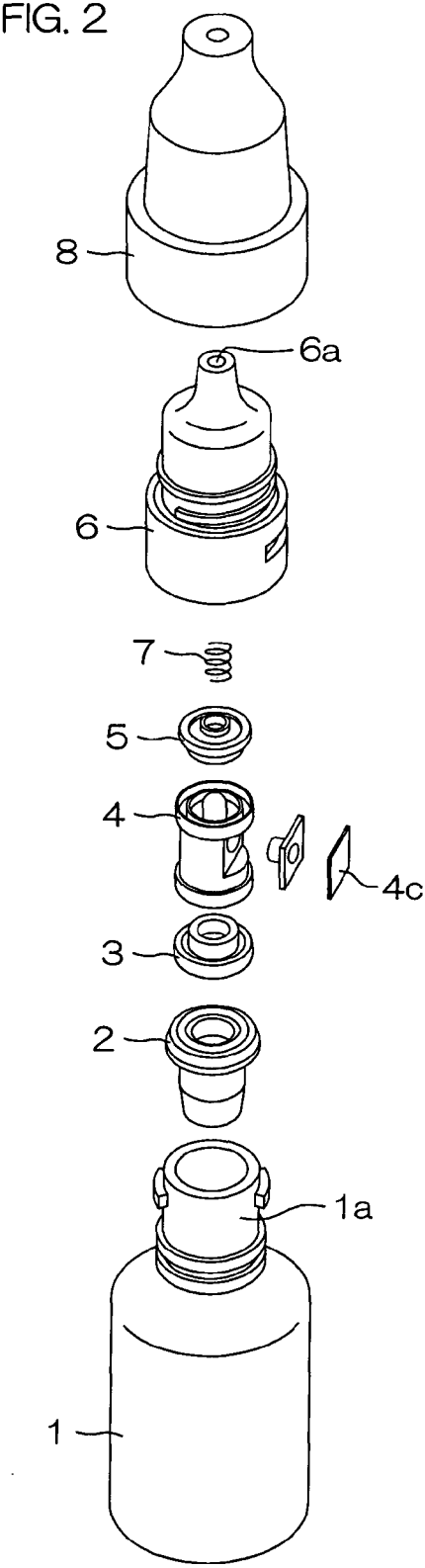
FIG. 2 is an exploded perspective view of the container for eye drops.

FIG. 1 is a side sectional view showing a container for eye drops according to an embodiment of the present invention. FIG. 2 is an exploded perspective view thereof.

The container for eye drops includes a container main body 1 for housing a medicinal solution. The container main body 1 is a hollow cylindrical-shaped container having an opening portion at its upper portion, and is preferably made of a transparent resin. Transparency is desired in order to visually check the amount of the medicinal solution housed inside. Also the container main body 1 itself is pressed and deformed by hand, and is thus formed of a material having flexibility and restorability. Examples of the resin to form the container main body 1 that can be mentioned include polyethylene (PE), polypropylene (PP), cyclic polyolefin (COP), and polyethylene terephthalate (PET). Particularly, PE and PP have high flexibility, and are therefore suitable for a container that houses a medicinal solution, such as a container for eye drops.

In an opening portion 1a of the container main body 1, an inner lid 2 to arrange a check valve 3 is mounted. This inner lid 2 is formed of a hollow columnar body so as to be fitted to the opening portion 1a of the container main body 1, and at an upper end portion of the inner lid 2, a flange 2a to contact the opening portion of the container main body 1 when the inner lid 2 is pushed in so as to position the inner lid 2 is formed.

The foregoing check valve 3 is a ring-shaped soft member to be placed on an upper surface of this flange 2a. A ring-shaped opening periphery of the check valve 3 is arranged standing upward (referred to as a standing portion 3a), and a lower end of a hole provided in the center of the standing portion 3a has a slightly reduced opening diameter, and forms a valve element 3b of the check valve 3. For the material of the check valve 3, a material having a low hardness and high flexibility is used. Examples of the material of the check valve 3 that can be mentioned include rubber-like substances such as thermoplastic elastomers, natural rubber, silicone rubber, isoprene rubber, butyl rubber, butadiene rubber, and fluorine-containing rubber.

Further, at an upper portion of the check valve 3, an inner cylindrical body 4 having a medicinal solution passage P which is communicated with the container main body 1 and for discharging the medicinal solution housed in the container main body 1 when the container main body 1 is pressed and deformed is arranged. At a tip of a bottom portion of the inner cylindrical body 4, a nozzle-shaped base end tube 4a of a smaller diameter is formed downward. As a result of the valve element 3b of the foregoing check valve 3 being mounted around the base end tube 4a, leaking of the medicinal solution in the interior of the container main body 1 to wet a filter portion 4c is prevented when the container main body 1 is pressed and the internal pressure of the container main body 1 reaches a positive pressure. Also when the internal pressure of the container main body 1 reaches a negative pressure, air that has passed through the filter portion 4c flows in the interior of the container main body 1 through the check valve 3 as will be described later, so that the negative internal pressure of the container main body 1 is eliminated to return to normal pressure.

In addition, a marginal portion of the check valve 3 is directly abutted against and closely fitted to an inner side surface of an inner cap 6.

At an outer side surface of the inner cylindrical body 4, an air intake 4b is formed which is communicated with the exterior of the container main body 1, and introduces outside air into the interior of the container main body 1 when the container main body 1 is released from pressing and restored. This air intake 4b is communicated with a gap A formed between an outer peripheral surface of the inner cylindrical body 4 and an outer peripheral surface of the opening portion 1a and an inner peripheral surface of the inner cap 6, and outside air flows in, through this gap A, to the air intake 4b.

Moreover, at the air intake 4b, a hydrophobic filter portion 4c for purifying outside air to flow in is provided. This filter portion 4c is for preventing the medicinal solution from being contaminated with bacteria and the like.

A gap B is provided at an exit side of the air intake 4b, and this gap B is communicated with the foregoing check valve 3 (although it seems as if the gap B were not communicated in the sectional view of FIG. 1, but the gap B is actually communicated via a passage provided on the outer side surface of the inner cylindrical body 4). Therefore, as described above, when the internal pressure of the container main body 1 reaches a negative pressure, air that has passed through the filter portion 4c flows in the interior of the container main body 1 through the check valve 3 via the gap B, so that the negative internal pressure of the container main body 1 is eliminated.

These gaps A and B form an "air flow passage." Air that is present in the gap A is air not via the filter portion 4c, and air that is present in the gap B is air free from contamination that has passed through the filter portion 4c.

At a center portion of an upper end of the inner cylindrical body 4, formed is a stopper member 4d disposed by fixing to the inside of the medicinal solution passage P and having a tip portion 4e, the tip portion 4e of which has a circular cross section when viewed from a medicinal solution discharge direction F, that is, a stopper member 4d of a solid structure in a columnar rod shape is formed. The tip portion 4e is formed at an end portion of a downstream side (an upper side of the paper) in the medicinal solution discharge direction F of the stopper member 4d. This stopper member 4d does not particularly need to be deformed, and is thus preferably formed of a hard resin such as polycarbonate, polyethylene terephthalate (PET), and polyacetal.

Also, in terms of the shape of the tip portion 4e of the stopper member 4d, the present invention can also be carried out so that the tip portion 4e has a cross section other than a circular cross section when viewed from the medicinal solution discharge direction F. The cross section may be in an elliptical shape and a square shape.

When the cross-sectional shape of the tip portion 4e is a circular shape, as will be described later by using figures, the three-dimensional shape of the tip portion 4e is a hemispherical shape, a conical shape, or an inverted conical shape. When the cross-sectional shape of the tip portion 4e is a square shape, the three-dimensional shape of the tip portion 4e is a square pyramidal shape, and when the cross-sectional shape of the tip portion 4e is an ellipse, the three-dimensional shape of the tip portion 4e is an elliptic conical shape.

Further, on the tip portion 4e of the stopper member 4d located at the upper end of the inner cylindrical body 4, a pressure valve 5 is placed which makes contact from a downstream side in the medicinal solution discharge direction F, from the top to the bottom of the paper, is formed with an opening, and having elasticity. This pressure valve 5 has a ring-shaped projection portion 5c at its peripheral portion, and as a result of this projection portion 5c being fitted in a ring-shaped fitting groove formed in a peripheral portion of the upper end of the inner cylindrical body 4, the pressure valve 5 is supported and fixed. In addition, the supporting structure of the pressure valve 5 is not limited to this, and may adopt any structure as long as the pressure valve 5 can be supported and fixed to the inside of the medicinal solution passage P.

It suffices that the pressure valve 5 has an opening shape matched with the cross-sectional shape of the tip portion 4e of the stopper member 4d in order to improve adhesion. It suffices that the opening shape of the pressure valve 5 is provided as a circular shape when the cross-sectional shape of the tip portion 4e is a circular shape, and the opening shape of the pressure valve 5 is provided as a square shape when the cross-sectional shape of the tip portion 4e is a square shape, and the opening shape of the pressure valve 5 is provided as an ellipse when the cross-sectional shape of the tip portion 4e is an ellipse.

It is assumed in the following that the cross-sectional shape of the tip portion 4e is a circular shape and the opening shape of the pressure valve 5 is also a circular shape.

The pressure valve 5 is a ring-shaped soft member. The opening formed at a center portion of this ring has an opening diameter slightly smaller than the diameter of the tip portion 4e of the stopper member 4d, and is in close contact with the tip portion 4e. The pressure valve 5 is a pressure-operated valve with a backflow preventing mechanism, which opens to let the medicinal solution flow downstream in the discharge direction (upward direction F in FIG. 1) when the exterior reaches a negative pressure, but never opens even when the exterior reaches a positive pressure, that is, prevents backflow of the medicinal solution.

Figure 3:
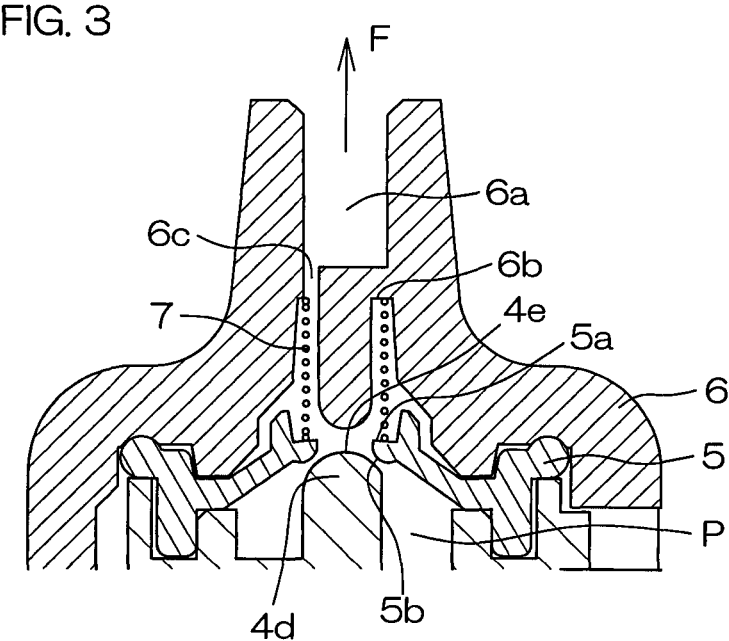
FIG. 3 is a sectional view illustrating a state where a pressure valve opens when a container main body is pressed.

The pressure valve 5 is usually abutted against the stopper member 4d to close the opening, but when the pressure of the interior of the container becomes higher than the atmospheric pressure such as when using the container for eye drops, a gap is produced between the stopper member 4d and the pressure valve 5 surrounding the same to discharge the medicinal solution housed in the container to the exterior of the container main body 1 through the opening of the pressure valve 5 (refer to FIG. 3).

However, when the internal pressure of the interior of the container becomes equal to or lower than the atmospheric pressure, the pressure valve 5 quickly returns to its original shape, and closely fits the tip portion 4e of the stopper member 4d to close a flow passage formed at the opening of the pressure valve 5. Therefore, the pressure valve 5 prevents the medicinal solution from entering into the container (refer to FIG. 4).

The material of the pressure valve 5 is required to be easily deformed by a fluid pressure. Therefore, a material having a low hardness and high flexibility is used. Examples of the material of the pressure valve 5 that can be mentioned include rubber-like substances such as thermoplastic elastomers, natural rubber, silicone rubber, isoprene rubber, butyl rubber, butadiene rubber, fluorine-containing rubber, and halogenated butyl rubber. Since it is particularly important not to bond to the stopper member 4d naturally, it is desirable to use a styrene-based or an olefine-based thermoplastic elastomer.

Moreover, the inner cap 6 having a spout 6a for a medicinal solution is mounted so as to surround the inner cylindrical body 4. An outer cap 8 that can be screwed onto the outer periphery of the inner cap 6 is further provided, and when the outer cap 8 is mounted, the spout 6a is blocked (refer to FIG. 1). When applying eye drops, the outer cap 8 is removed and the medicinal solution is caused to fall in drops from the spout 6a for a medicinal solution.

Figure 4:
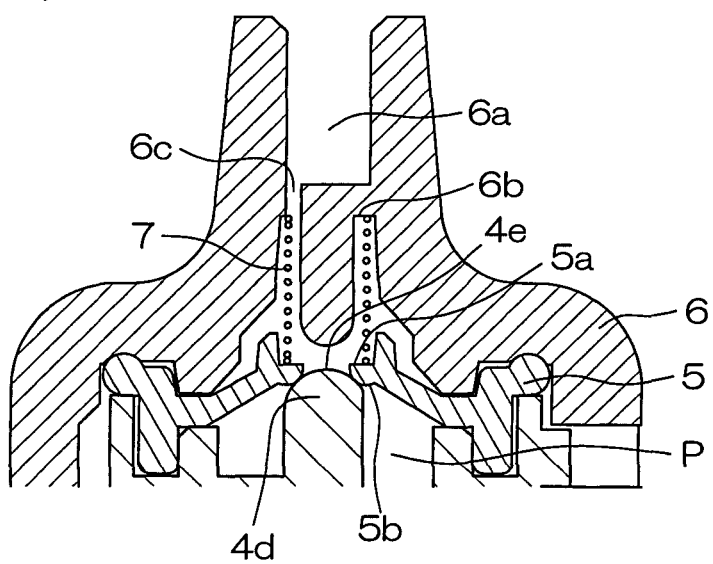
FIG. 4 is a sectional view illustrating a state where the pressure valve is closed.

At a downstream side in the medicinal solution discharge direction F further than the pressure valve 5 in the medicinal solution passage P, a biasing member 7 is arranged. The biasing member 7 consists of, for example, a spring coil as shown in FIG. 3 and FIG. 4 or a stretch tube 7a having elasticity integrated with a pressure valve as in FIG. 22, and abuts against a peripheral surface 5a of the opening of the pressure valve 5 to bias the pressure valve 5 in a direction opposite to the medicinal solution discharge direction F. By this biasing, the opening of the pressure valve 5 is reliably pressed to contact the tip portion 4e of the stopper member 4d so as to assist the pressure valve 5 to closely fit the tip portion 4e of the stopper member 4d when the internal pressure of the interior of the container is lower than the atmospheric pressure. For the material of the spring coil, a material with elasticity and chemical resistance, for example, stainless steel is used. In the case of the tube 7a integrated with a pressure valve shown in FIG. 22, it suffices to use the same raw material as that of the pressure valve.

An end of the biasing member 7 opposite to the end to press the pressure valve 5 is supported and fixed to a ring-shaped groove 6b formed at a downstream side in the medicinal solution discharge direction F further than the pressure valve 5 in the medicinal solution passage P. Supporting force of this groove 6b can assist the biasing member 7 to press the pressure valve 5. In addition, a cut-away 6c for creating the medicinal solution passage P is formed at a part of the ring-shaped groove 6b.

If the elastic force of the biasing member 7 is too strong, a large pressing force is required for the container main body 1 when the medicinal solution housed inside is discharged from the spout 6a. If the elastic force is too weak, the force at which the pressure valve 5 closely fits the tip portion 4e of the stopper member 4d is weak, leakage of the solution is likely to occur, and backflow from the spout 6a is easily caused. Therefore, it is necessary to adjust the hardness of the container main body 1 and the required opening pressure of the valve element in consideration that usually, the pressing force of the thumb and fingers of a person who presses the container main body 1 when applying eye drops is 2N (newtons) or more and 20N or less.

The internal pressure is increased if the volume of a space inside the container main body 1 is reduced, by pressing from the medicinal solution passage P to make a peripheral portion 5b of the opening of the pressure valve 5 and the stopper member 4d out of contact so as to cause opening. An internal pressure of 0.05 MPa can be achieved by providing the volume of the interior space of the container main body 1 as 50%, and an internal pressure of 0.02 MPa can be achieved by providing the volume as 80%, but the volume of the inner space increases as the solution falls in drops, and it becomes difficult to reduce the volume, and thus it is desirable to conduct design so that the valve element is opened at a pressure as low as possible.

Figure 18:
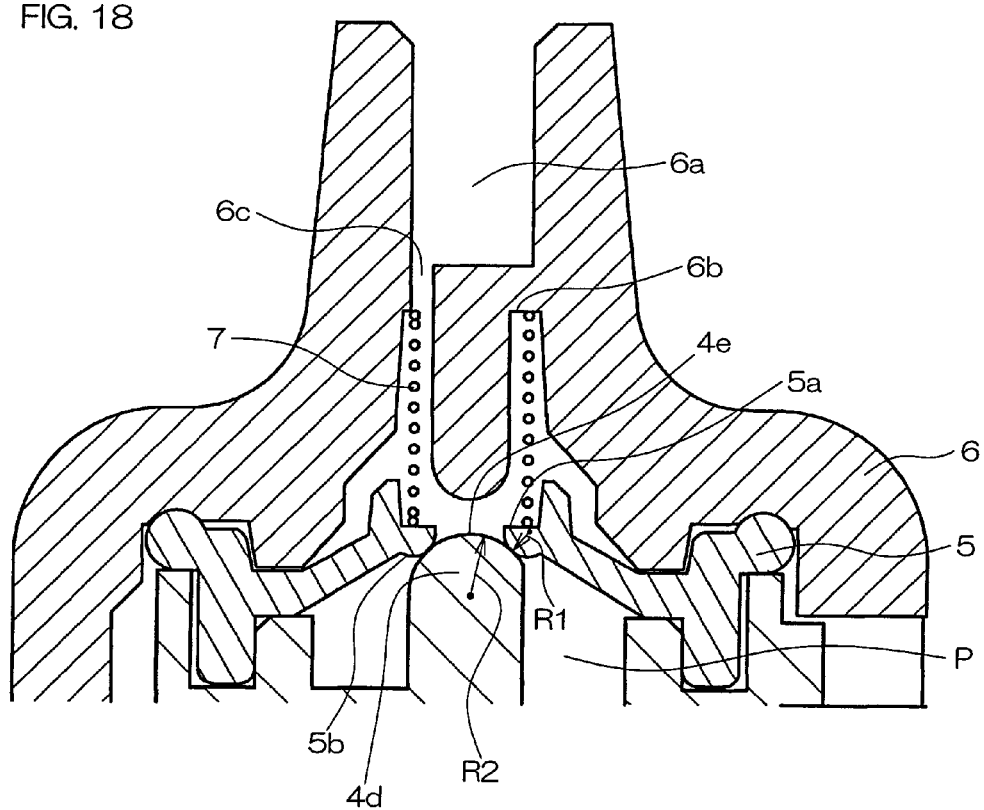
FIG. 18 is a view showing a radius R1 of curvature of the pressure valve and a radius R2 of curvature of the tip portion of the stopper member.

In the embodiment of the present invention, the opening pressure can be set by changing the elasticity of the biasing member 7. In consideration of the spatial capacity of the container, it suffices to set the elastic force of the biasing member 7 so that the medicinal solution is discharged by applying pressure in any range of 0.001 MPa to 0.05 MPa, preferably, 0.003 MPa to 0.03 MPa, and more preferably, 0.005 MPa to 0.03 MPa. Specifically, it suffices to set the elastic force of the biasing member 7 to a force of 4 g weight to 20 g weight (gram-weight), preferably, 5 g weight to 10 g weight, and more preferably, 6 g weight to 7 g weight. Further, it is desirable for the peripheral portion 5b of the opening of the pressure valve 5 that its part that contacts the tip portion 4e of the stopper member 4d has a curvature like that of a confectionery doughnut so as to make line contact in a ring shape with the tip portion 4e. As shown in the sectional view of FIG. 18, it suffices that the radius R1 of the curvature is 0.05 mm to 3 mm, preferably, 0.1 mm to 2 mm, and more preferably, 0.2 mm to 1 mm. Moreover, it is also necessary that the tip portion 4e of the stopper member 4d has curvature, and it suffices that the radius R2 of the curvature is in a range of 0.3 mm to 4 mm, preferably, 0.5 mm to 2 mm, and more preferably, 0.7 mm to 1 mm. Smoothness and flatness of each contact surface are also necessary in order to maintain airtightness of contact between the peripheral portion 5b and the tip portion 4e.

Setting as such allows the medicinal solution to fall in drops with a normal pressing force of a thumb and fingers that press the container main body 1 when applying eye drops, and completely preventing mixing of bacteria from the discharge side of the valve element, so that sterility can be maintained.

This biasing member 7 also has a role of absorbing variation in the shape of the pressure valve 5, deviation in the positional relationship between the pressure valve 5 and the stopper member 4d, and a positional deviation in the assembled state of the pressure valve 5.

Figure 5:
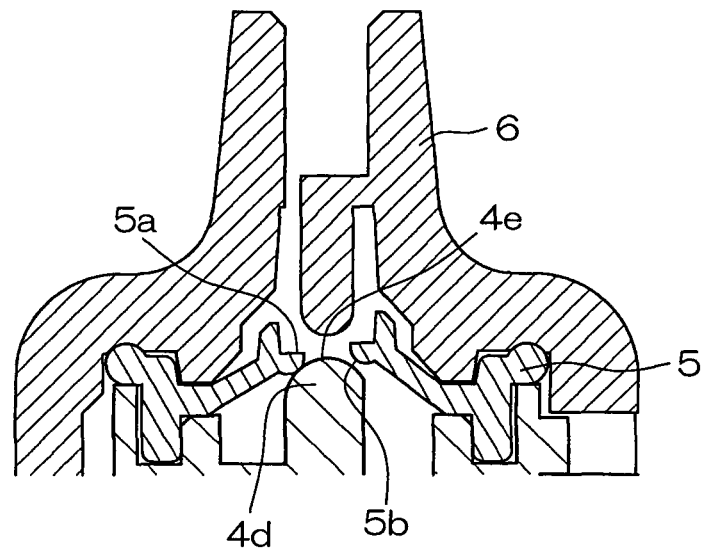
FIG. 5 is a sectional view showing a state that the pressure valve is not normally abutted against a stopper member because the pressure valve is distorted in shape.

FIG. 5 is a figure showing a state where only the elasticity of the pressure valve 5 is insufficient for press-contact against the tip portion 4e of the stopper member 4d because the pressure valve 5 is distorted in shape or the assembled state of the pressure valve 5 is inaccurate, and there is a gap produced between the opening of the pressure valve 5 and the tip portion 4e.

Figure 6:
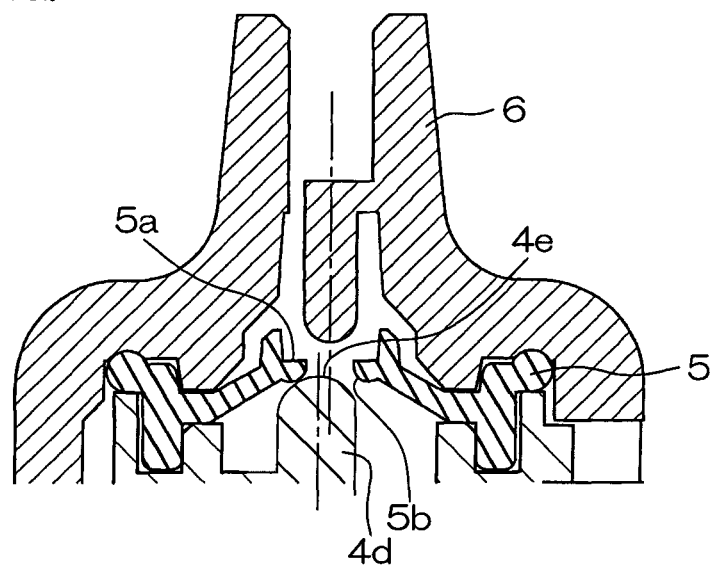
FIG. 6 is a sectional view showing a state that the pressure valve is not normally abutted against a stopper member because the pressure valve and the stopper member are off-center from each other.

FIG. 6 shows a state where there is a deviation in the central axis between the pressure valve 5 and the stopper member 4d, and there is a gap produced between the opening of the pressure valve 5 and the tip portion 4e.

In either case, by providing the biasing member 7 in accordance with the present invention, making the biasing member 7 abut against the peripheral surface 5a of the opening of the pressure valve 5, and pressing the pressure valve 5 in a direction opposite to the discharge direction F of the medicinal solution, as shown in FIG. 4, the pressure valve 5 is completely closely fitted to the stopper member 4d so as to eliminate any gap between the opening of the pressure valve 5 and the tip portion 4e of the stopper member 4d. Accordingly, variation in the shape of the pressure valve 5, deviation in the positional relationship between the pressure valve 5 and the stopper member 4d, and a positional deviation in the assembled state of the pressure valve 5 can be absorbed.

Hereinafter, the operation when applying eye drops of the container for eye drops will be described by using FIG. 3 and FIG. 4.

In a state where the main body 1 of the container for eye drops is not pressed, as shown in FIG. 4, the biasing member 7 biases by its elasticity the pressure valve 5 downward, and the opening of the pressure valve 5 is closed.

When the main body 1 of the container for eye drops is operated by pressing, the pressure valve 5, due to a difference in pressure, acts against the force of the biasing member 7, and as shown in FIG. 3, moves in the discharge direction F of the medicinal solution, and as a result, the opening of the pressure valve 5 opens, and the eye drop solution is discharged from the opening of the pressure valve 5. At this time, since the check valve 3 (FIG. 1) is closed, the medicinal solution in the container never leaks out of the check valve 3.

When pressing of the main body 1 of the container for eye drops is released, the restoring force of the pressure valve 5 and the biasing force of the biasing member 7 act together, and the opening of the pressure valve 5 is closed. The main body 1 of the container for eye drops reaches a negative pressure in its interior with the purpose of being restored, and under this condition, outside air passes through the filter portion 4c and flows in the interior of the main body 1 of the container for eye drops. Outside air is cleaned by the action of the filter portion 4c, which is as described above.

By the above operation, the medicinal solution in the container main body 1 can be caused to fall in drops from the spout 6a with a slight force to directly press the container main body 1, and the container main body 1 can take in air through the filter portion 4c when the container main body 1 is restored.

Now, the relationship between the shape of the opening of the pressure valve 5 and the three-dimensional shape of the tip portion 4e of the stopper member 4d will be described. It is necessary for the opening of the pressure valve 5 to be closely fitted with the tip portion 4e of the stopper member 4d so as not to have a gap, and the following examples can be mentioned.

Figure 7:
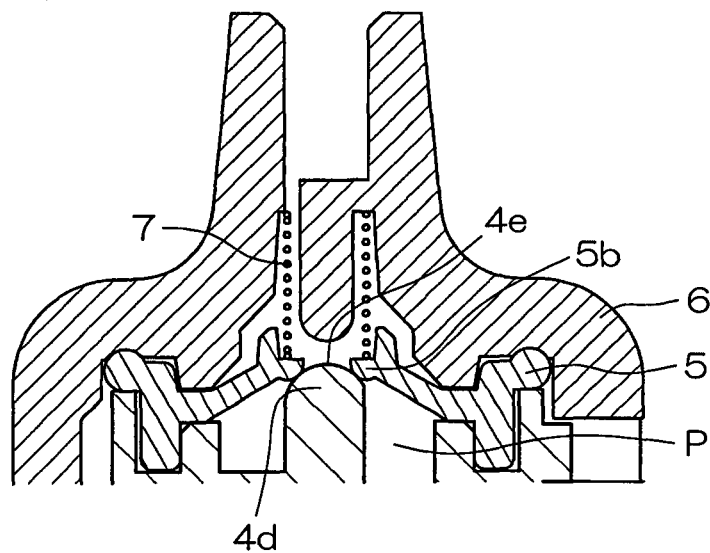
FIG. 7 is a sectional view showing a contact state between a tip portion of the stopper member and an opening of the pressure valve.

FIG. 7 shows a case where the tip portion 4e of the stopper member 4d has a hemispherical shape, and the longitudinal sectional shape of the peripheral portion 5b of the opening of the pressure valve 5 is a circular shape (doughnut hole). Accordingly, the tip portion 4e and the peripheral portion 5b of the opening make line contact by convex curved surfaces, and can contact along one virtual circumferential line of the tip portion 4e, which enables close fitting.

Figure 8:
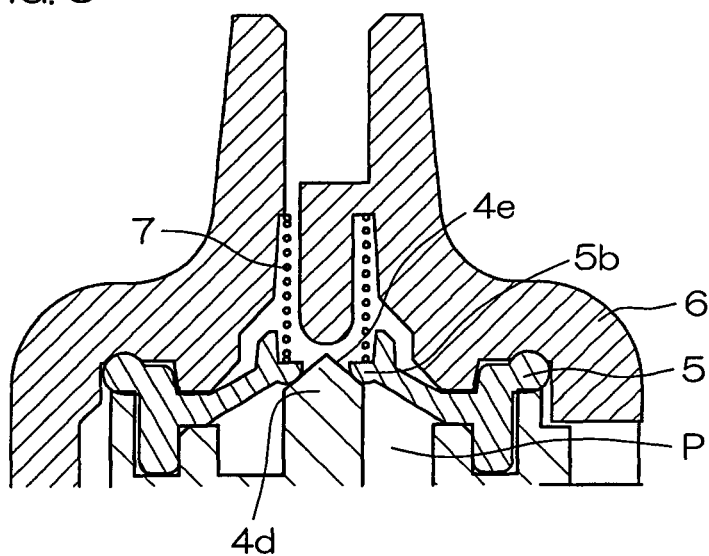
FIG. 8 is a sectional view showing a contact state between a tip portion of the stopper member and an opening of the pressure valve.

FIG. 8 shows a case where the tip portion 4e of the stopper member 4d has a conical shape, and the longitudinal sectional shape of the peripheral portion 5b of the opening is a circular shape. In this case, the tip portion 4e and the peripheral portion 5b of the opening make line contact by a conical surface and a convex curved surface and can contact along one virtual circumferential line of the tip portion 4e, which enables close fitting.

Figure 9:
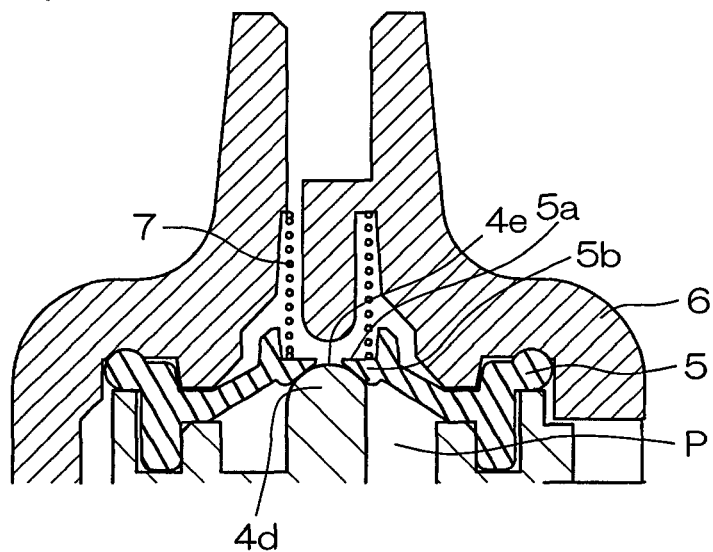
FIG. 9 is a sectional view showing a contact state between a tip portion of the stopper member and an opening of the pressure valve.

FIG. 9 shows a case where the tip portion 4e of the stopper member 4d has a hemispherical shape, and the longitudinal sectional shape of the peripheral portion 5b of the opening is a concave surface shape like being hollowed out in an inverted conical shape. In this case, the tip portion 4e of the opening and the peripheral portion 5b of the opening make contact by a concave curved surface and a convex curved surface and can contact along a virtual circumferential band having a fixed width of the tip portion 4e, which enables closer fitting.

In all of FIG. 7 to FIG. 9, a part of the peripheral portion 5b of the opening of the pressure valve 5 that contacts the tip portion 4e of the stopper member 4d can abut against the tip portion 4e of the stopper member 4d without a gap, which can exhibit an effect of preventing leakage of the medicinal solution. Moreover, deviation between the central line of the stopper member 4d and the central line of the pressure valve 5 can also be prevented.

Figure 10:
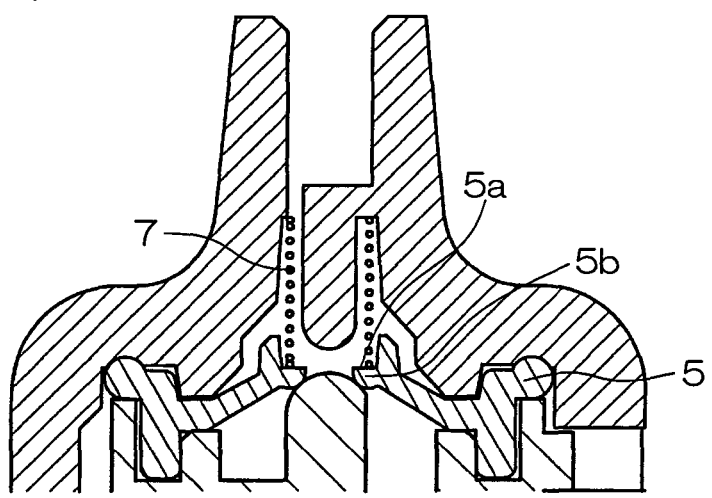
FIG. 10 is a sectional view showing a state where a biasing member is directly abutted against a peripheral portion of the opening of the pressure valve.

For the container for eye drops of the present invention, various other modifications can be made. In the foregoing description, the biasing member 7, as shown in FIG. 10, biases the pressure valve 5 by directly abutting against the peripheral surface 5a of the opening of the pressure valve 5, but another member may be interposed between the biasing member 7 and the peripheral portion 5b of the opening of the pressure valve 5.

Figure 11:
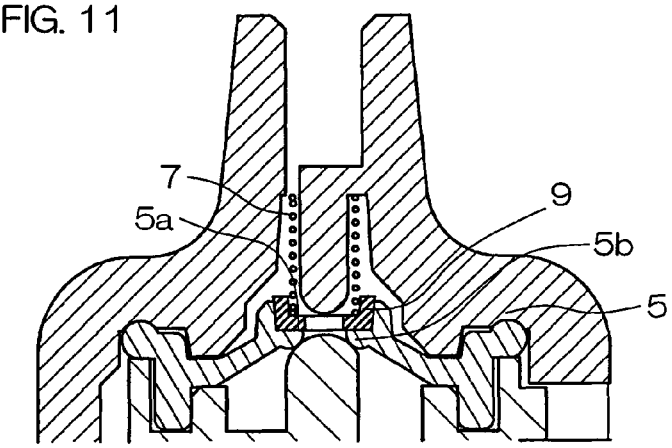
FIG. 11 is a sectional view showing a relationship where a biasing member abuts against a peripheral portion of the opening of the pressure valve via a seat.
Figure 12:
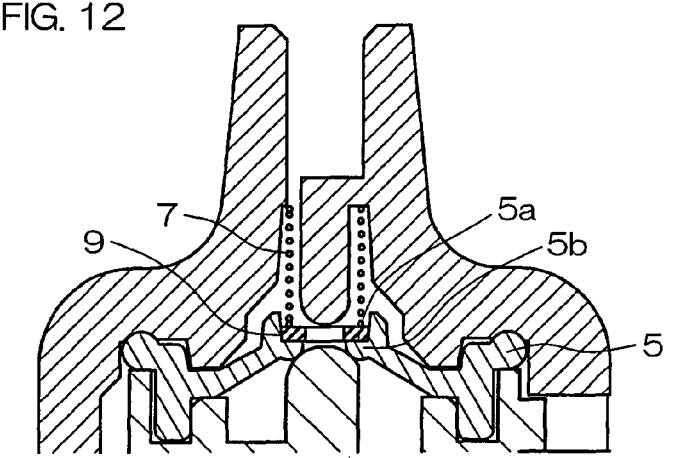
FIG. 12 is a sectional view showing a relationship where a biasing member abuts against a peripheral portion of the opening of the pressure valve via a seat.

FIG. 11 and FIG. 12 show a ring-shaped seat 9 arranged on the peripheral surface 5a of the opening of the pressure valve 5. There is a difference that the seat 9 is raised at its periphery in FIG. 11, while the seat 9 of FIG. 12 is in a planar shape.

Figure 13:
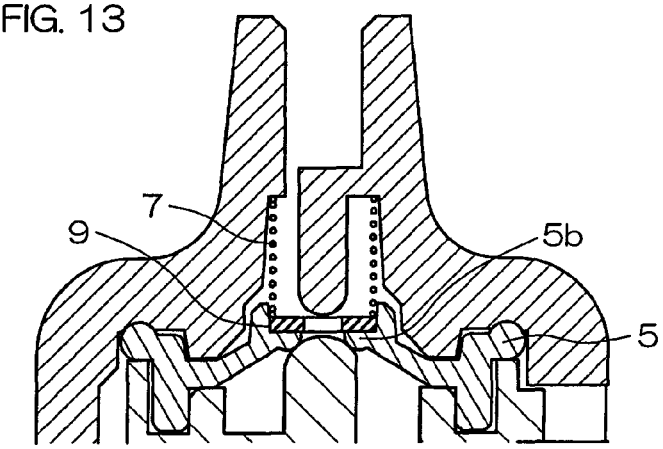
FIG. 13 is a sectional view showing a relationship where a biasing member abuts against a peripheral portion of the opening of the pressure valve via a seat.

FIG. 13 shows a seat 9 that is increased in diameter or area to correspond to a large spring diameter of the biasing member 7. As in these modifications, as a result of interposing a seat 9 between the biasing member 7 and the pressure valve 5, the seat 9 relieves a large local pressure to be applied to the peripheral portion 5b of the opening of the pressure valve 5, and an averaged pressure is applied to the pressure valve 5, so that deformation and damage to the pressure valve 5 can be avoided.

Figure 14:
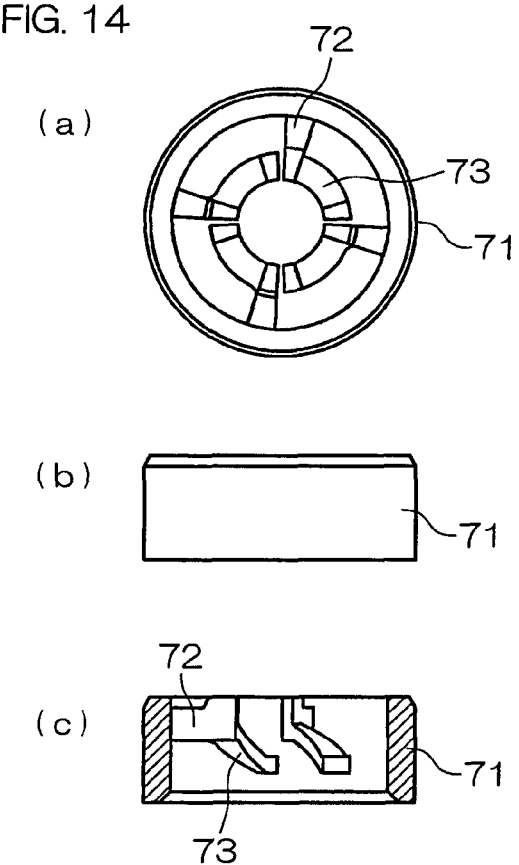
FIG. 14 includes a plan view (a), a side view (b), and a side sectional view (c) showing an example of a spiral spring as a biasing member.
Figure 15:
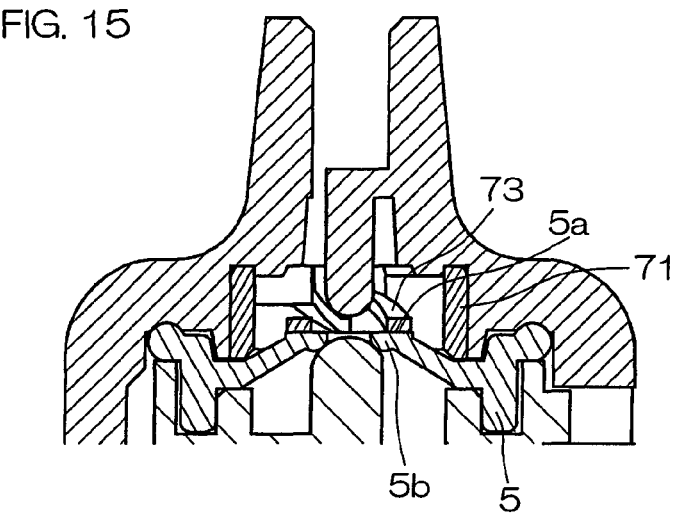
FIG. 15 is a sectional view showing a state where the peripheral portion of the opening of the pressure valve is pressed by a spiral spring.

Also in the foregoing description, a spring coil is exemplified as the biasing member 7, but the biasing member 7 is not limited to this. FIG. 14 shows an example using a spiral spring. For this spiral spring, projection pieces 72 are provided extending from a plurality of spots of a cylindrical-shaped outer frame 71 toward a center portion. From the end of each projection piece 72, a presser plate 73 is provided extending obliquely along the same circumferential direction. Each presser plate 73 is provided with elasticity so that the end of each presser plate 73 can hold down the pressure valve 5. Accordingly, as shown in FIG. 15, the peripheral surface 5a of the opening of the pressure valve 5 can be pressed downward.

Figure 16:
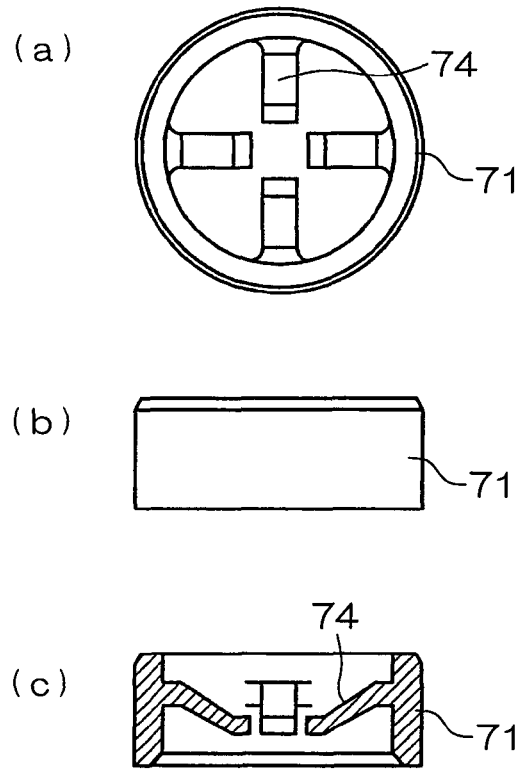
FIG. 16 includes a plan view (a), a side view (b), and a side sectional view (c) showing an example of a cross spring as a biasing member.
Figure 17:
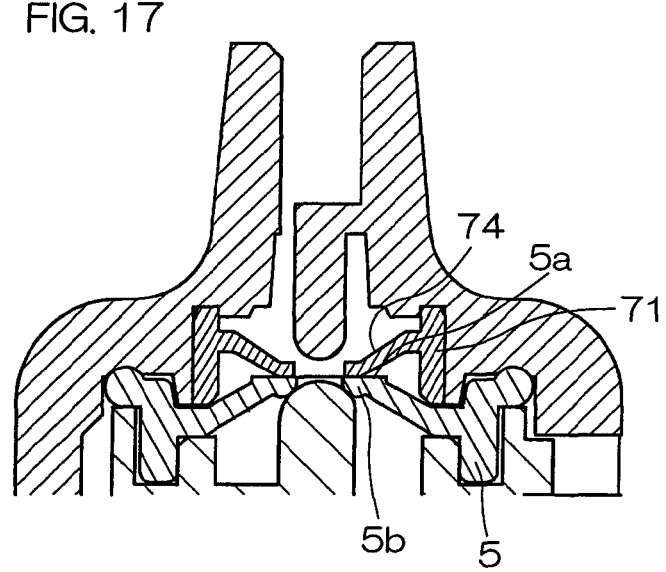
FIG. 17 is a sectional view showing a state where the peripheral portion of the opening of the pressure valve 5 is pressed by a cross spring.

FIG. 16 shows a shape using a cross spring. A plurality of elastic pieces 74 project from a cylindrical-shaped outer frame 71 toward a center portion. Each elastic piece 74 has elasticity so that the end of each elastic piece 74 can hold down the peripheral portion 5b of the opening of the pressure valve 5. Accordingly, as shown in FIG. 17, the peripheral surface 5a of the opening of the pressure valve 5 can be thereby pressed downward.

Next, a container for eye drops according to another embodiment of the present invention will be described with reference to FIG. 19 to FIG. 21. This container for eye drops basically has a structure similar to that of the container for eye drops of FIG. 1 to FIG. 4. In the following, only parts different from those of the container for eye drops of FIG. 1 to FIG. 4 will be described.

Figure 19:
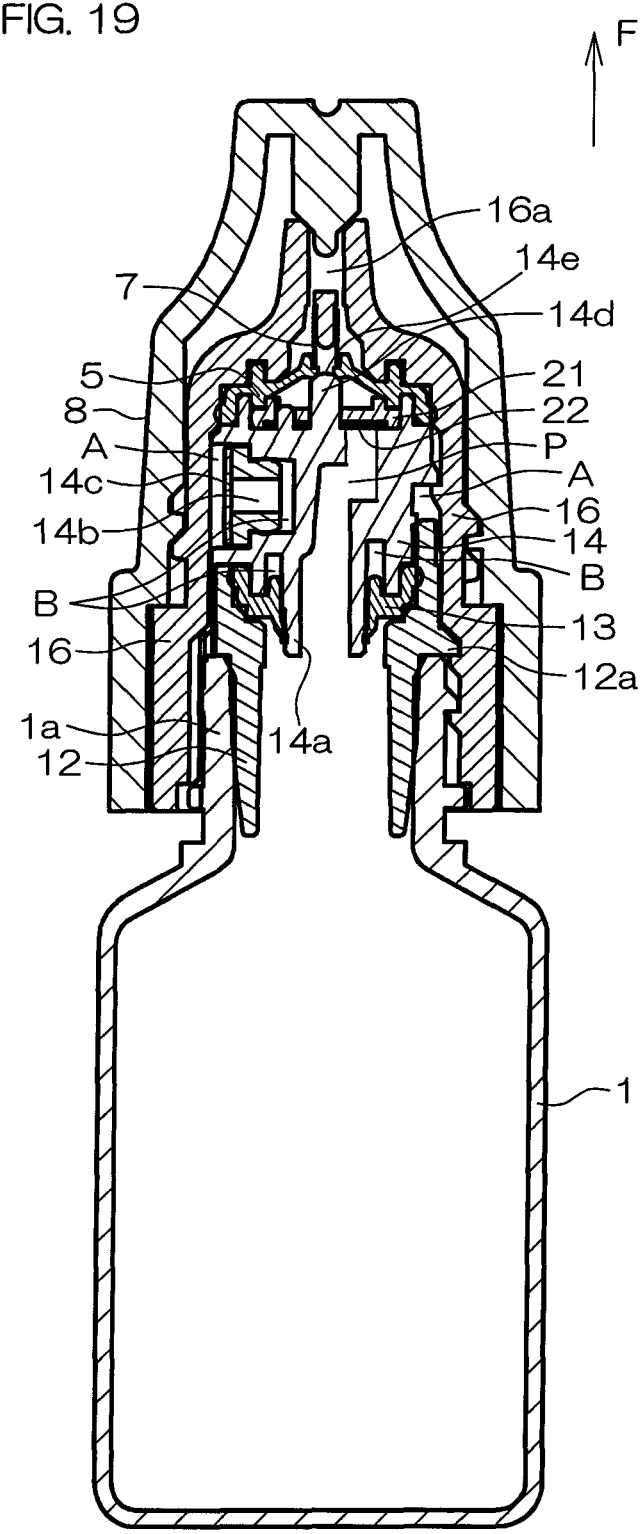
FIG. 19 is a side sectional view showing a container for eye drops according to another embodiment of the present invention.

FIG. 19 is a side sectional view showing a container for eye drops according to another embodiment of the present invention. FIG. 20 is an exploded perspective view thereof.

The container for eye drops includes a container main body 1 which is a hollow cylindrical-shaped container having an opening portion at its upper portion. In an opening portion 1a of the container main body 1, an inner lid 12 to arrange a check valve 13 is mounted. This inner lid 12 is formed of a hollow columnar body so as to be fitted to the opening portion 1a of the container main body 1, and at an upper end portion of the inner lid 12, a flange 12a to contact the opening portion of the container main body 1 when the inner lid 12 is pushed in so as to position the inner lid 12 is formed. The check valve 13 is placed on an upper end surface of the inner lid 12. A marginal portion of the check valve 13 is not directly abutted against an inner peripheral surface of an inner cap 16.

Further, at an upper portion of the check valve 13, an inner cylindrical body 14 having a medicinal solution passage P is arranged. At a tip of a bottom portion of the inner cylindrical body 14, a nozzle-shaped base end tube 14a of a smaller diameter is formed downward, and a valve element of the foregoing check valve 13 is mounted around the base end tube 14a, which is the same as in the container for eye drops of FIG. 1.

At a side surface of the inner cylindrical body 14, an air intake 14b having a filter portion 14c is formed, and this air intake 14b is communicated with a gap A formed between an outer peripheral surface of the inner cylindrical body 14 and an outer peripheral surface of the inner lid 12 and the inner peripheral surface of the inner cap 16, and outside air flows in, through this gap A, the filter portion 14c, the air intake 14b, and a gap B, to the container main body 1. Air that passes the gap B is air via the filter portion 14c.

At a downstream side in the medicinal solution discharge direction further than the check valve 13 in the medicinal solution passage P, specifically, at an upper end surface of the inner cylindrical body 14, a filter portion 22 in order to block foreign substances and particles permissible for eye drops from reaching the pressure valve 5 and a filter presser 21 for mounting this filter portion 22 are disposed.

Moreover, through-holes are provided at a center portion of the filter portion 22 and a center portion of the filter presser 21, respectively, and through these through-holes, a tip portion 14e of a stopper member 14d is inserted upward from below, that is, from an upstream side toward a downstream side in the medicinal solution discharge direction F. Further, a pressure valve 5 is placed at the upper end of the inner cylindrical body 14, which is the same as in the container for eye drops of FIG. 1.

Figure 21:
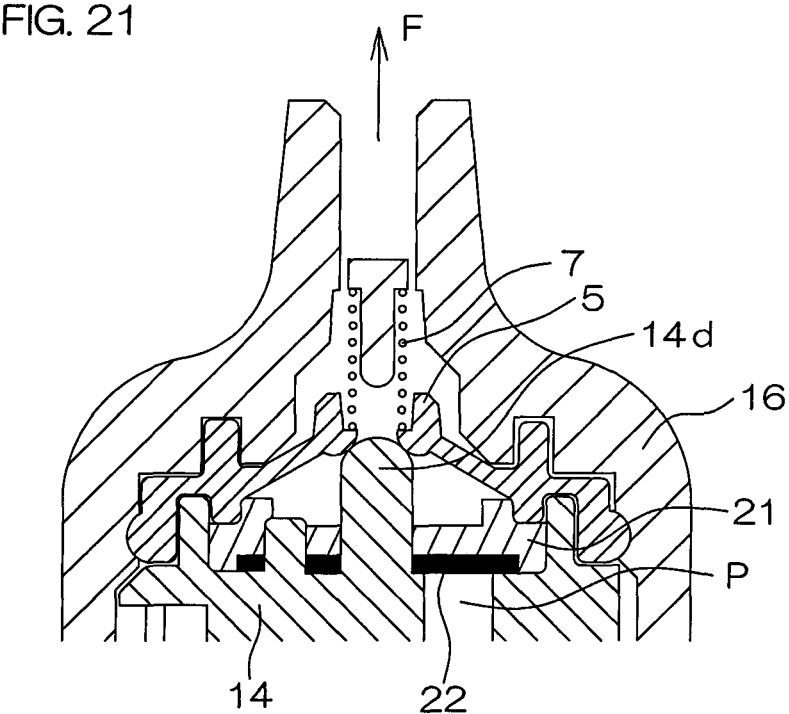
FIG. 21 is a partially enlarged sectional view of a vicinity of the biasing member and the pressure valve of the container for eye drops.

FIG. 21 is a partially enlarged sectional view of a vicinity of the biasing member 7 and the pressure valve 5 of a container for eye drops. It shows a state where the main body 1 of the container for eye drops is not pressed, the biasing member 7 biases by its elasticity the pressure valve 5 downward, and the opening of the pressure valve 5 is closed.

When the main body 1 of the container for eye drops is operated by pressing, the pressure valve 5, due to a difference in pressure, acts against the force of the biasing member 7, and moves in the discharge direction F of the medicinal solution, and as a result, the opening of the pressure valve 5 opens, and the eye drop solution is discharged from the opening of the pressure valve 5. At this time, since the medicinal solution has passed through the filter portion 22, foreign substances and particles (for example, minute pieces of resin that were produced when the inner lid 12 and the inner cylindrical body 14 were mounted on the main body 1 of the container for eye drops) permissible for eye drops can be blocked from reaching the pressure valve or trapped by the filter portion 22.

Figure 22:
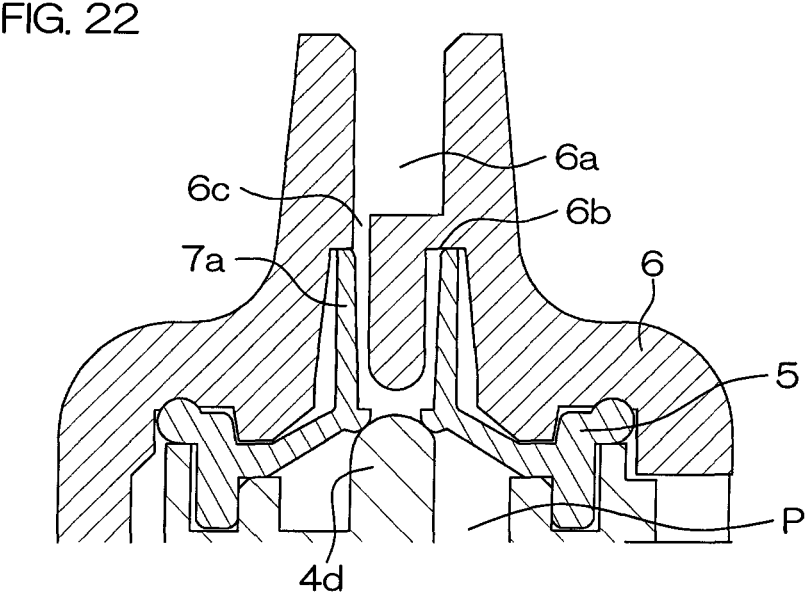
FIG. 22 is a side sectional view showing a container for eye drops according to still another embodiment, for which the biasing member is molded integrally with an opening portion of the pressure valve.

FIG. 22 is a partially enlarged sectional view of a vicinity of the pressure valve 5 of a container for eye drops according to still another embodiment, for which the biasing member 7 is molded integrally with an opening portion of the pressure valve 5. A stretch tube 7a having elasticity integrated with the pressure valve 5 is used as a biasing member. In addition, the biasing member can be in any shape as long as it can reliably press the opening of the pressure valve 5 to contact the tip portion 4e of the stopper member 4d. The biasing member may be, for example, a bellows-like tube, in addition to the straight cylindrical-shaped tube as shown in FIG. 22.

REFERENCE SIGNS LIST

1 Container main body
1a Opening portion
2, 12 Inner lid
2a, 12a Flange
3, 13 Check valve
3a Standing portion
3b Valve element
3c Upper space of valve element
4, 14 Inner cylindrical body
4a, 14a Base end tube
4b, 14b Air intake
4c, 14c Filter portion
4d, 14d Stopper member
4e, 14e Tip portion
5 Pressure valve
5a Peripheral surface of opening
5b Peripheral portion of opening
6, 16 Inner cap
6a, 16a Spout
7, 7a Biasing member
8 Outer cap
22 Filter portion (second)
A, B Gap (air flow passage)
P Medicinal solution passage

The invention claimed is:

1. A container for eye drops comprising:
a flexible and restorable container main body for housing a medicinal solution;
a medicinal solution passage communicating with the container main body, for discharging the medicinal solution housed in the container main body when the container main body is pressed and deformed;
a stopper member fixed to an inside of the medicinal solution passage, having a tip portion at a downstream side in a medicinal solution discharge direction, the tip portion having a predetermined-shaped cross section when viewed from the medicinal solution discharge direction;
a pressure valve arranged, in the medicinal solution passage, at a downstream side in the medicinal solution discharge direction further than the tip portion of the stopper member, and being formed with an opening in a center portion thereof having a predetermined-shaped cross section that contacts the tip portion; and
a biasing member provided, in the medicinal solution passage, at a downstream side in the medicinal solution discharge direction further than the pressure valve, for biasing the pressure valve in a direction opposite to the medicinal solution discharge direction by abutting against a peripheral portion of the opening of the pressure valve,
wherein the pressure valve is made of a material to that is easily deformed by a fluid pressure, and a peripheral portion of the pressure valve is supported and fixed to the inside of the medicinal solution passage.

2. The container for eye drops according to claim 1, wherein the tip portion of the stopper member has a circular cross section when viewed from the medicinal solution discharge direction.

3. The container for eye drops according to claim 2, wherein the tip portion of the stopper member has a hemispherical shape.

4. The container for eye drops according to claim 2, wherein of the opening of the pressure valve, a part that contacts the tip portion of the stopper member makes line contact in a ring shape with the tip portion of the stopper member, and the contact part has a circular longitudinal section.

5. The container for eye drops according to claim 2, wherein the tip portion of the stopper member has a conical shape.

6. The container for eye drops according to claim 5, wherein of the opening of the pressure valve, a part that contacts the tip portion of the stopper member makes line contact in a ring shape with the tip portion of the stopper member, and the contact part has a circular longitudinal section.

7. The container for eye drops according to claim 1, wherein the biasing member is directly abutted against a peripheral surface of the opening of the pressure valve.

8. The container for eye drops according to claim 1, wherein the biasing member is abutted against a peripheral surface of the opening of the pressure valve via a seat.

9. The container for eye drops according to claim 1, wherein the biasing member is molded integrally with the opening of the pressure valve.

10. The container for eye drops according to claim 1, further comprising: an air flow passage communicating with an exterior of the container main body causing outside air to flow into an interior of the container main body when the container main body is released from pressing and restored; and
a filter portion provided in the air flow passage, for purifying outside air flowing in.

11. The container for eye drops according to claim 10, further comprising a check valve portion provided in the air flow passage, and closes the air flow passage when an internal pressure of the container main body reaches a positive pressure.

12. The container for eye drops according to claim 1, wherein a second filter portion is disposed, in the medicinal solution passage, at an upstream side in the medicinal solution discharge direction further than the pressure valve.

13. A container for eye drops comprising:
a flexible and restorable container main body for housing a medicinal solution;
a medicinal solution passage communicating with the container main body, for discharging the medicinal solution housed in the container main body when the container main body is pressed and deformed;
a stopper member fixed to an inside of the medicinal solution passage, having a tip portion at a downstream side in a medicinal solution discharge direction, the tip portion having a predetermined-shaped cross section when viewed from the medicinal solution discharge direction;
a pressure valve arranged, in the medicinal solution passage, at a downstream side in the medicinal solution discharge direction further than the tip portion of the stopper member, and being formed with an opening having a predetermined-shaped cross section that contacts the tip portion; and
a biasing member provided, in the medicinal solution passage, at a downstream side in the medicinal solution discharge direction further than the pressure valve, for biasing the pressure valve in a direction opposite to the medicinal solution discharge direction by abutting against a peripheral portion of the opening of the pressure valve, wherein the biasing member is directly abutted against a peripheral surface of the opening of the pressure valve.

14. The container for eye drops according to claim 13, further comprising: an air flow passage communicating with an exterior of the container main body causing outside air to flow into an interior of the container main body when the container main body is released from pressing and restored; and a filter portion provided in the air flow passage, for purifying outside air flowing in.

15. The container for eye drops according to claim 14, further comprising a check valve portion provided in the air flow passage, and closes the air flow passage when an internal pressure of the container main body reaches a positive pressure.

16. A container for eye drops comprising:

a flexible and restorable container main body for housing a medicinal solution;

a medicinal solution passage communicating with the container main body, for discharging the medicinal solution housed in the container main body when the container main body is pressed and deformed;

a stopper member fixed to an inside of the medicinal solution passage, having a tip portion at a downstream side in a medicinal solution discharge direction, the tip portion having a predetermined-shaped cross section when viewed from the medicinal solution discharge direction;

a pressure valve arranged, in the medicinal solution passage, at a downstream side in the medicinal solution discharge direction further than the tip portion of the stopper member, and being formed with an opening having a predetermined-shaped cross section that contacts the tip portion; and a biasing member provided, in the medicinal solution passage, at a downstream side in the medicinal solution discharge direction further than the pressure valve, for biasing the pressure valve in a direction opposite to the medicinal solution discharge direction by abutting against a peripheral portion of the opening of the pressure valve, wherein the biasing member is abutted against a peripheral surface of the opening of the pressure valve via a seat.

17. The container for eye drops according to claim 16, further comprising: an air flow passage communicating with an exterior of the container main body causing outside air to flow into an interior of the container main body when the container main body is released from pressing and restored; and a filter portion provided in the air flow passage, for purifying outside air flowing in.

18. The container for eye drops according to claim 17, further comprising a check valve portion provided in the air flow passage, and closes the air flow passage when an internal pressure of the container main body reaches a positive pressure.

\* \* \* \* \*

UNITED STATES PATENT AND TRADEMARK OFFICE
CERTIFICATE OF CORRECTION

| | |
|---|---|
| PATENT NO. | : 8,783,521 B2 |
| APPLICATION NO. | : 13/321806 |
| DATED | : July 22, 2014 |
| INVENTOR(S) | : Shinichi Ishikawa et al. |

It is certified that error appears in the above-identified patent and that said Letters Patent is hereby corrected as shown below:

In the Claims

Claim 1, col. 13, line 60, "a material to that is" should read --a material that is--.

Signed and Sealed this
Third Day of March, 2015

Michelle K. Lee
*Deputy Director of the United States Patent and Trademark Office*